United States Patent [19]
Burke

[11] Patent Number: 6,049,005
[45] Date of Patent: Apr. 11, 2000

[54] PROCESS TO PREPARE A PENTENOIC ACID ANHYDRIDE

[75] Inventor: Patrick M. Burke, Wilmington, Del.

[73] Assignees: DSM N.V., Heerlen, Netherlands; E. I. du Pont de Nemours, Del.

[21] Appl. No.: 08/946,055

[22] Filed: Oct. 7, 1997

[51] Int. Cl.[7] .................................................. C07C 51/56
[52] U.S. Cl. ........................................ 562/891; 562/890
[58] Field of Search ..................... 562/890, 891

[56] References Cited

U.S. PATENT DOCUMENTS

| | | | |
|---|---|---|---|
| 3,641,137 | 2/1972 | Fenton | 562/522 |
| 4,325,834 | 4/1982 | Bartish et al. | 252/429 R |
| 4,781,868 | 11/1988 | Langerbeins | 260/549 |
| 4,824,817 | 4/1989 | Drent | 502/154 |
| 5,756,828 | 5/1998 | Arnoldy et al. | 560/207 |

FOREIGN PATENT DOCUMENTS

| | | | |
|---|---|---|---|
| 273 489 | 11/1987 | European Pat. Off. | C07C 67/38 |
| 428 979 | 5/1991 | European Pat. Off. | C07C 57/03 |
| 3544765 | 6/1987 | Germany | C07C 51/56 |
| 47-47005 | 11/1972 | Japan | B01J 11/00 |

OTHER PUBLICATIONS

*Derwent Abstract, DE 3544764.
**Derwent Abstract, JP 47–47005.

*Primary Examiner*—Johann Richter
*Assistant Examiner*—Rosalynd Keys
*Attorney, Agent, or Firm*—Pillsbury Madison & Sutro Intellectual Property Group

[57] ABSTRACT

Process to prepare a pentenoic acid anhydride in the pressence of a catalyst comprising palladium and an organic phosphine ligand, wherein the corresponding alkoxycarbonyl butene is reacted with carbon monoxide at a temperature between 50 and 130° C. and that the phosphine is a monodentate phosphine or a bidentate phosphine.

11 Claims, No Drawings

PROCESS TO PREPARE A PENTENOIC ACID ANHYDRIDE

The invention relates to a process to prepare a pentenoic acid anhydride in the presence of a catalyst comprising palladium and an organic phosphine ligand.

Such a process is described in EP-A-273489. This patent publication describes that butadiene can be reacted with an acid and carbon monoxide to an anhydride of pentenoic acid. This reaction is performed in the presence of a catalyst system comprising palladium, a bidentate phosphine ligand and preferably an acid co-catalyst. The examples of this patent only describe the reaction of butadiene with ethanol and carbon monoxide to ethyl pentenoate at 150° C. using a catalyst system comprising palladium, 1,4 di(diphenylphosphino)butane and 2,4,6-trimethylbenzoic acid. A carboxylic acid promoter such as 2,4,6-trimethylbenzoic acid is necessary for achieving high selectivities to ethyl pentenoate.

A disadvantage of this process is that when preparing the anhydride of pentenoic acid under the conditions as exemplified in EP-A-273489 (for the preparation of ethyl pentenoate) a low rate of reaction is observed. Because the catalyst system is unstable during the reaction a low reaction rate will result in relativelly more catalyst loss per mole product produced.

The object of this invention is a process to prepare a pentenoic acid anhydride compound at a higher reaction rate and under conditions where the catalyst is more stable.

This object is achieved when the corresponding alkoxycarbonyl butene is reacted with carbon monoxide at a temperature between 50 and 130° C. and that the phosphine ligand is a mono- or bidentate phosphine ligand.

Using the process according to the invention up to 10 times higher reaction rates to the anhydride compound can be achieved compared to when starting from butadiene. Further, lower temperatures can be used than exemplified in EP-A-273489. By performing the reaction at lower temperatures the rate of degradation of the phosphine ligand will furthermore reduced.

Japanese patent publication, JP-B-72047005, describes a process to prepare unsaturated carboxylic acid anhydride compounds by carbonylation starting from an alkoxycarbonyl alkene compound. The catalyst is a palladium/phosphine containing catalyst. Alkoxycarbonyl butene is however not mentioned in the description. Only allylic dienes, e.g. 1-acetoxy-2,7-octadienen, and terminal hindered allylic acetates, e.g. methallyl acetate are taught as starting materials in this publication. Furthermore the reported selectivity and conversion to the carboxylic acid anhdyride is low. A high yield and reaction rate was therefore unexpected when starting from alkoxycarbonyl butene.

The alkoxycarbonyl butene is preferably a compound according to the following formula:

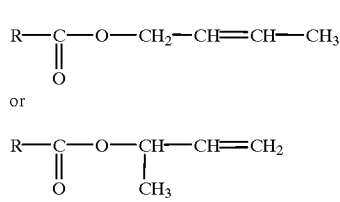

in which R is an alkyl group having 1–20 carbon atoms. Examples of alkyl groups are methyl, ethyl, n-propyl, isopropyl, n-butyl, tert-butyl, pentyl, cyclopentyl, cyclohexyl and hexyl. Preferably acetoxy butene (R=methyl) is used as starting compound.

The alkoxycarbonyl butene can be prepared from butadiene and the corresponding carboxylic acid in the pressence of a suitable catalyst. The catalyst is preferably an acid catalyst, and more preferably a heterogeneous acid catalyst. Examples of possible acid catalysts are sulfuric acid, sulfonic acids, for example methane sulfonic acid or trifluoromethane sulfonic acid, trifluoro acetic acid, phosphoric acid, or heterogeneous acid catalysts, for example strongly acidic ion-exchange resins, for example sulfonated polystyrene-divinylbenzene ion-exchange resins.

Butenyl acetates can also be prepared by the oxidative acetoxylation of 2-butene over a heterogeneous palladium containing catalyst.

The phosphine ligand used in the process according to the invention can be a monovalent or multivalent phosphine ligand. Preferred monodentate phosphine ligand can be described by the following general formula, $P(R^1)_3$, wherein $R^1$ represent an optionally substituted organic group in which three groups can be the same or different. This organic group is preferably a $C_1$–$C_{20}$ alkyl group, a $C_6$–$C_{18}$ aryl group or a cyclic group with 4–12 carbon atoms in which the ring of the cyclic group also contains one or more heteroatoms, for example nitrogen. Alkyl groups include, among others, methyl, ethyl, isopropyl, tert-butyl, cyclopentyl, cyclohexyl or cyclooctyl. Exemplary cyclic groups containing heteroatoms include, among others, 6-methyl-2-pyridyl and 4,6-dimethyl-2-pyridyl. Aryl groups include, for example, naphthyl, phenyl, benzyl, cumenyl, mesityl, tolyl and xylyl. The organic group can be substituted, for example, with halogen atoms, for example Cl, Br or F, or with $C_1$–$C_6$ alkyl, $C_6$–$C_{18}$ aryl, $C_1$–$C_6$ alkoxy, carboxy, carbalkoxy, acyl, trihalogenmethyl, cyano, dialkylamino, sulphonylalkyl or alkanoyloxy groups. Substituents can be groups with electron withdrawing or electron donating properties. Preferably one group $R^1$ is an alkyl group while the remaining groups are aryl groups. The use of such ligands result in high rate of reaction.

Monodentate phosphine ligands include, for instance, tri-p-tolylphosphine, tri-p-methoxyphenylphosphine, diphenylpentylphosphine, dimethylphenylphosphine, ethyldiphenyl phosphine or cyclohexyldiphenylphosphine.

Preferred bidentate phosphine ligands are represented by,

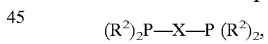

in which $R^2$ represents an optionally substituted organic group, in which the four groups $R^2$ can be the same or different. $R^2$ can be a group as described for $R^1$. X is an organic bridging group having 3–20 carbon atoms.

Furthermore two $R^2$ groups bonded to one P-atom can form one divalent organic group, for example a diaryl group or a $C_2$–$C_{20}$ alkylene group. An exemplary alkenyl group is butenyl. Examples of diaryl groups include diphenyl and dinaphthyl groups. The substituents for the organic groups $R^2$ can be the same as described above for the monodentate phosphine ligands. Preferably one or more of groups $R^2$ are aliphatic groups. Examples of possible aliphatic and aryl groups are described above for $R^1$.

Divalent organic bridging groups (X) include $C_{24}$–$C_{10}$ alkylidene groups, for example tetramethylene, pentamethylene or trans-1,2-cyclobutene; and $C_6$–$C_{20}$ divalent arylgroups such as, for example, dinaphythyl or diphenyl. Preferably the number of carbon atoms in the shortest chain connecting the phosphorus atoms is at least three. In this chain one hetero atom may be present, for example nitrogen, oxygen or sulfur.

The bidentate phosphine ligands include, among others, 1,4-bis(diphenylphosphino)butane, 2,3-dimethyl-1,4-bis (diphenylphosphino)butane, 1,4-bis(n-butylphenylphosphino)butane, 1,4-bis (dicyclohexylphosphino)butane, 1,4-bis (cyclohexylphenylphosphine)butane, 1,4-bis(di-p-methoxyphenylphosphino)-butane, 2,2'-bis (diphenylphosphino)biphenyl, 2,3-bis(diphenyl-phosphino) naphthalene, 2,2-dimethyl-4,5-bis(diphenylphosphino)-dioxolane, trans-[(bicyclo[2.2.1]-heptane-2,3-diyl)bis (methylene)]-bis[diphenylphosphine], trans-[(bicyclo[2.2.2] octane-2,3-diyl)bis(methylene)]-bis[diphenylphosphine], and 2,2'-bis(diphenylphosphino)-1,1'-binapthyl.

The optimal molar ratio of phosphine ligand to palladium will depend on the specific phosphine ligand used in the process according to the invention. This ratio can be between about 1:1 and 100:1, preferably between about 1:1 and 10:1 and more preferably between 1:1 and 3:1. The palladium phosphine ratio has been found to be a critical value in order to obtain optimal results. Preferably this ratio is so choosen that no more than two of the co-ordination sites of the palladium can be blocked by the ligand. Bidentate phosphines having short chain bridges according to the invention, like bis(diphenylphosphino)butane, can coordinate the two sites of the palladium with one phosphine molecule. Bidentate phosphine molecules having more flexible bridging groups, i.e. with at least 5 carbon atoms in the chain linking the two P-atoms, can only co-ordinate one site of the palladium. The optimal phosphine palladium ratio fo the first ligand class will have an optimal value around 1:1 (mol/mol), while the second ligand class will have an optimal value around 2:1 (mol/mol). Depending on the manner of co-ordination between the ligand and palladium the optimal ratio for bidentate phosphine ligands will be between about 1:1 and about 2:1. Monodentate phosphines can naturally only co-ordinate one site of the palladium and therefore have an optimal ratio of around about 2:1 mol phosphine/mol palladium.

All inert solvents are in principle suitable as an additional solvent, although it is also possible to use an excess of one of the reactants or (by-) products in such an amount that a suitable liquid phase is formed. Examples of (by-) products are $C_9$-esters and other high boiling by-products. Examples of inert solvents are sulfoxides and sulfones, such as for instance, dimethyl sulfoxide, diisopropyl sulfone; aromatic solvents, such as benzene, toluene, xylene; esters, such as methyl acetate, methyl valerate, pentenoate esters and butyrolactone; ketones, such as acetone or methylisobutyl ketone; ethers such as anisole, trioxanone, diphenyl ether and diisopropyl ether; and mixtures of these solvents. Preferably, diphenyl ether is used as additional solvent.

The reaction can optionally be performed in the presence of the carboxylic acid corresponding to the alkoxycarbonyl group. Better results have been obtained when performing the reaction in the absence of such additional carboxylic acid. Preferably the process is performed in the absence of any additional added carboxylic acid, because this results in a more simple process in contrast with the process of EP-A-273489 which required an additional acid co-catalyst.

The palladium can be added to the reaction mixture as a heterogeneous palladium compound or as a homogeneous palladium compound. However, homogeneous systems are preferred. Since palladium in situ forms a complex with the phosphine ligand, the choice of the initial Pd compound is in general not critical. Homogeneous palladium compounds include, for instance, palladium salts of, for instance, nitric acid, sulfonic acid, alkane carboxylic acids with not more than 12 carbon atoms or hydrogen halogenides (Cl, Br, I). Metallic palladium can also be used. Exemplary homogeneous palladium compounds include $PdCl_2$, $PdBr_2$, $PdI_2$, $Na_2PdI_4$, $K_2PdI_4$, $PdCl_2(benzonitrile)_2$ and bis (allylpalladium chloride). Another group of suitable halogen-free palladium compounds are palladium complexes such as palladium acetylacetonate ($Pd(acac)_2$), Pd(II) acetate, palladiumnitrate $Pd(NO_3)_2$, o-tolyl phosphine palladium, and di-palladium-tris-(dibenzylideneacetone)$Pd_2$ $(dba)_3$. An exemplary of a heterogeneous palladium compound is a palladium compound on an ion exchanger such as, for example an ion exchanger containing carboxylic acid groups. Ion exchangers containing carboxylic acid groups are commercially available under the brand names Amberlite IRC 50 and Amberlite IRC 84 (Rohm & Haas). Another heterogeneous catalyst is an immobilized phosphine on carrier catalyst, in which the palladium forms a complex with the immobilized phosphine (phosphine being the ligand of the catalyst system). Carriers include polystyrene, polyacrylamide, silica, alumina, silica-alumina or zeolite support.

Preferably the reaction is performed using a substantially halide-free palladium catalyst.

The palladium concentration in the reaction mixture is preferably as high as possible because the greater will be the rate of reaction per unit of reactor volume. The upper limit for a homogeneous catalyst system will normally be determined by the solubility of palladium in the reaction mixture and will, for example, depend on the specific palladium compound used as discussed above. This upper limit can easily be determined by one skilled in the art. However, the process according to the invention may also be performed with a homogeneous catalyst system in the presence of solid palladium compounds.

The temperature is between 50 and 130° C. and preferably between 80 and 110° C. The pressure can vary between 1 MPa and 100 MPa, although it is preferably greater than 3 MPa and more preferably greater than 3.5. An upper limit is not critical, although a very high pressure is disadvantageous because the process equipment will become very expensive. A practical and preferred upper limit is therefore about 10 MPa.

The carbon monoxide can be used in a pure form or diluted with an inert gas such as, for example, nitrogen, rare gases or carbon dioxide. In general, more than 5% hydrogen is undesirable, since this can cause hydrogenation of the alkoxycarbonyl butene under the carbonylation conditions.

The reaction is preferably performed in the absence of carboxylic acids, e.g. acetic acid, because these compounds tend to inhibit the carbonylation reaction.

Preferably a continuous process is used. An example of reactor system for a continuous process is a series of continuously stirred tank reactors (CSTR) in which the catalyst system, a possible solvent, Compound 1 and carbon monoxide are fed to a first reactor. The various ratios according to the process of the invention can be maintained by controlling the feed rate of the various reactants and catalyst components.

The pentenoic acid ahydrides will be obtained as a mixture of 2-, 3- and 4-pentenoic acid anhydrides. These anhydride compounds can advantageously be converted to pentenoic acid or pentenoate esters using process known to one skilled in the art. By reacting the anhydride with an acid the pentenoic acid and the corresponding anhydride will be formed. By reacting with an alcohol the corresponding pentenoate ester and an ester by-product will be formed. By reacting the anhydride with water pentenoic acid and the acid corresponding to the alkoxycarbonyl group will be formed. The thus obtained acid by-product can advantageously be used to prepare the alkoxycarbonyl butene from butadiene as described above.

The products obtained by the process according to the invention can be used as precursor in processes to prepare adipic acid and ε-caprolactam, which are valuable Nylon intermediates.

The invention shall be elucidated by the following non-limiting examples.

EXAMPLE I

A 120 mL mechanically stirred Hastelloy-C autoclave was charged with a solution of 0.056 g (0.25 mmole) of palladium acetate, 0.21 g (0.48 mmole) of 1,5-bis (diphenylphosphino)pentane, in 88 mL diphenyl ether solvent. The solution was heated to a temperature of 100 C under an initial pressure of 300 psi (2.07 MPa). The reaction was initiated by injecting a solution of 5.7 g (50 mmole) of crotyl acetate (1-acetoxybutene-2 or CrOAc) and 1.0 g ortho-dichlorobenzene (ODCB, GC internal standard) in 4.7 mL diphenyl ether and adjusting the total pressure to 500 psi (3.45 MPa). Carbon monoxide was continuously fed to the autoclave from a reservoir so as to maintain the total pressure constant at 500 psi (3.45 MPa).

Samples were removed at intervals for GC analysis for crotyl esters and butadiene. The GC analysis indicated about 69% of the butenyl acetate (crotyl acetate and its isomer 3-acetoxybutene-1) was consumed in 30 minutes and 89% in 60 minutes. The final product, after 20 hours at 100° C., was predominantly the mixed anhydrides of 2- and 3-pentenoic and acetic acids together with smaller amounts of butadiene, acetic anhydride, bis-3-pentenoic anhydrides, crotyl pentenoates and free pentenoic acids.

The total carbonylation yield was determined by esterification of the anhydrides and acids with methanol-p-toluenesulfonic acid followed by a second GC analysis for methyl esters. The following results were obtained from the 2 GC analyses:

| | Moles per mole CrOAc Charged | | | |
|---|---|---|---|---|
| Time (Min.) | Butadiene | Butenyl Acetates | M3P | M2P(1) |
| 30 | 13.1 | 29.4 | 41.0 | 0.8 |
| 60 | 17.5 | 11.2 | 54.5 | 2.6 |
| 1200 | 11.5 | 0.7 | 31.5 | 42.0 |

(1)M3P = methyl 3-pentenoate, M2P = methyl 2-pentenoate (1) M3P=methyl 3-pentenoate, M2P=methyl 2-pentenoate
The first order rate constant for the conversion of all C4 precursors (butenyl esters and butadiene) was 1.74 Hr-1, corresponding to a turnover frequency of 252 moles converted per mole of palladium per hour.

EXAMPLE II

The experiment in Example 1 was repeated except that Crotyl acetate was replaced by 3-acetoxbutene-1. The GC analysis indicated about 74% butenyl acetate (3-acetoxybutene-1+crotyl acetate) conversion in 30 minutes and 85% conversion in 60 minutes. Esterification and GC analysis as in Example 1 gave the following results:

| | Moles per mole CrOAc Charged | | | |
|---|---|---|---|---|
| Time (Min.) | Butadiene | Butenyl Acetates | M3P | M2P |
| 30 | 14.2 | 25.7 | 46.1 | 1.0 |
| 60 | 18.4 | 9.0 | 58.7 | 2.8 |
| 1260 | 8.6 | 0.5 | 30.6 | 47.1 |

The first order rate constant for the conversion of all C4 precursors (butenyl esters and butadiene) was 1.96 Hr-1, corresponding to a turnover frequency of 282 moles converted per mole of palladium per hour.

Comparative Experiment A

The experiment in Example 1 was repeated except that Crotyl acetate was replaced by an equivalent amount of butadiene. The GC analysis indicated only 5.8% butadiene conversion in 30 minutes and 11% conversion in 60 minutes. Esterification and GC analysis as in Example 1 gave the following results:

| | Moles per mole CrOAc Charged | | | |
|---|---|---|---|---|
| Time (Min.) | Butadiene | Butenyl Acetates | M3P | M2P |
| 60 | 76.1 | 12.7 | 11.2 | 0.0 |
| 120 | 70.1 | 10.5 | 19.1 | 0.4 |
| 270 | 60.4 | 6.3 | 29.1 | 4.1 |
| 1200 | 51.2 | 2.8 | 23.6 | 22.6 |

EXAMPLE III

A 25 mL glass lined pressure vessel was charged with 5 mL of a solution containing 11.4 g (100 mmol) 3-acetoxybutene-1 (3AcB1), 0.112 g (0.5 mmol) of palladium acetate, 0.42 g (2.0 mmole of ethyl diphenylphosphine ligand (4/1 ligand/Pd ratio) and 1.0 g of o-dichlorobenzene (internal GC standard) in 100 mL diphenyl ether solvent. The pressure vessel was freed from air by purging first with nitrogen (twice) and then with CO (twice). The vessel was than pressurized to 900 psi (6.2 MPa) CO and heated to 90° C. with agitation for 2 hours. The pressure at 90 C was maintained at 900 psi (6.2 MPa) by feed CO from a reservoir. After 2 hours the heat was shut off and the pressure vessel was allowed to cool to room temperature. No insoluble palladium precipitates were present in the reaction solution. The excess gases were vented and the products were analyzed directly by GC for butadiene, butenyl acetates, crotyl pentenoates (Cr-Pent), 3-pentenoic actic anhydride and acetic anhydride. The product was also esterified with methanol using p-toluenesulfonic acid catalyst and the resulting solution was analyzed for methyl pentenoates. The following results were obtained:

| Before Esterification: (Moles/100 3AcB1 Charged) | |
|---|---|
| Butadiene | 1.6 |
| Butenyl Acetates | 15.1 |
| Crotyl Petenoates | 15.2 |
| 3-PA-acetic Anhydride | 39.4 |

-continued

| | |
|---|---|
| Acetic Anhydride | 23.2 |
| Acetic Acid | 3.9 |
| After Esterification: (Moles/100 3AcB1 Charged) | |
| M3P | 64.6 |
| M2P | 1.2 |

The conversion was thus 83.3% and the overall selectivity to pentenoic acid derivatives (methyl pentenoate and crotyl pentenoates) was 97.2%.

EXAMPLES IV–X

The experiment in Example III was repeated except that the phosphine ligand and the ratio of ligand to palladium were varied. Analysis of the product solutions before and after esterification gave the results summarized in Table 1:

TABLE 1

| Ex | Ligand | L/Pd | Conv | M3P | M2P | Cr-Pent |
|---|---|---|---|---|---|---|
| IV | Ph3P | 2 | 74.6 | 68.0 | 0.0 | 21.7 |
| V | Ph3P | 10 | 60.9 | 52.2 | 1.5 | 30.5 |
| VI | DPPP | 1 | 28.9 | 46.0 | 0.7 | 35.2 |
| VII | DPPB | 1 | 73.6 | 72.0 | 2.9 | 21.4 |
| VIII | Ph2PEt | 2 | 84.4 | 76.7 | 2.9 | 16.4 |
| IX | DPPPent | 2 | 85.6 | 75.2 | 8.6 | 12.6 |
| X | Ph2PCy | 1 | 74.5 | 55.0 | 5.2 | 22.4 |

Ph3P=triphenylphosphine
DPPP=1,3-bis(diphenylphosphino)propane
DPPB=1,4-bis(diphenylphosphino)butane
Ph2PEt=ethyldiphenylphosphine
DPPPent=1,5-bis(diphenylphosphino)pentane
Ph2PCy=Cyclohexyldiphenylphosphine The results illustrate the high selectivity to pentenoic acid derivatives using a Pd-catalyst and low ratio of monodentate or bidentate ligand to metal at low temperatures.

EXAMPLE XI

A 25 mL glass lined pressure vessel was charged with 5 mL of a solution containing 11.4 g (100 mmol) of 1-Acetoxybutene-2 (Crotyl acetate; CrOAc), 0.112 g (0.50 mmol) of palladium acetate, 1.04 g (2.36 mmole) of 1,5-bis(diphenylphosphino)pentane, 12.0 g (200 mmoles) acetic acid and 1.0 g of o-dichlorobenzene (internal GC standard) in 100 mL toluene. The pressure vessel was freed from air by purging first with nitrogen (twice) and then with CO (twice). The vessel was then pressurized to 500 psi (3.45 MPa) CO and heated to 120° C. with agitation for 3 hours. The pressure at 120° C. was maintained at 750 psi (5.17 MPa). After 3 hours the heat was shut off and the pressure vessel was allowed to cool to room temperature. GC analysis of the reaction solution showed the presence of 3-pentenoic acid and acetic anhydride. After hydrolysis of a 1 mL aliquot of the reaction solution with water (100 µl) at 80 C for 2 hours, the anhydride was completely hydrolyzed and the amount of 3-pentenoic acid increased. GC analysis showed 58% conversion of the acetoxybutenes and butadiene and a 91% selectivity to 3-pentenoic acid.

EXAMPLE XII

The experiment in example XI was repeated except that the solvent was acetic acid and the temperature was 140° C. GC analysis after hydrolysis showed 8.2% conversion and 93.6% selectivity to 3-pentenoic acid.

What is claimed is:

1. A process to prepare a pentenoic acid anhydride, comprising:

reacting an alkoxycarbonyl butene with carbon monoxide at a temperature between 50 and 130° C. in the presence of a catalyst comprising palladium and an organic phosphine ligand, wherein said phosphine ligand is a monodentate phosphine ligand or a bidentate phosphine ligand.

2. The process according to claim 1, wherein the temperature is between 80 and 110° C.

3. The process according to claim 1 or claim 2, wherein said process is conducted at a pressure of between 3–10 MPa.

4. The process according to claim 1 or claim 2, wherein the molar ratio of the phosphine ligand and palladium is between about 1:1 and 3:1.

5. The process according to claim 1 or claim 2, wherein the phosphine ligand is a compound represented by the formula:

$$P(R^1)_3 \text{ or } (R^2)_2P\text{—}X\text{—}P(R^2)_2$$

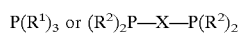

wherein $R^1$ and $R^2$ represents the same or two or more different optionally substituted organic groups, in which the organic group is a $C_1$–$C_{20}$ alkyl group, a $C_6$–$C_{18}$ aryl group or a cyclic group with 4–12 carbon atoms, in which the ring of the cyclic group also contains one or more heteroatoms, and X is an organic bridging group having 3–20 carbon atoms.

6. The process according to claim 1 or claim 2, wherein the phosphine ligand is a compound represented by the formula:

$$(R^2)_2P\text{—}X\text{—}P(R^2)_2$$

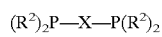

wherein $R^2$ represents the same or two or more different optionally substituted organic groups, in which the organic group is a $C_1$–$C_{20}$ alkyl group, a $C_6$–$C_{18}$ aryl group or a cyclic group with 4–12 carbon atoms, in which the ring of the cyclic group also contains one or more heteroatoms, and X is an organic bridging group having 3–20 carbon atoms wherein the number of C-atoms in the shortest chain connecting the two phosphorus atoms in the bridging group is at least three.

7. The process according to claim 1 or claim 2, wherein the monodentate ligand is represented by $P(R^1)_3$, wherein $R^1$ is a $C_1$–$C_{20}$ alkyl group, a $C_6$–$C_{18}$ aryl group or a cyclic group with 4–12 carbon atoms in which the ring of the cyclic group also contains one or more heteroatoms.

8. The process according to claim 1 or claim 2, wherein the alkoxycarbonyl butene is a compound according to the following formula:

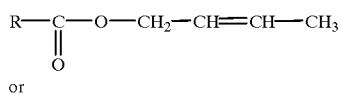

or

-continued

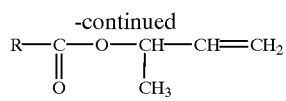

in which R is an alkyl group having 1–20 carbon atoms.

9. The process according to claim 8, wherein R is a methyl group.

10. The process according to claim 1 or claim 2, wherein the alkoxycarbonyl butene is prepared by reacting butadiene with acetic acid.

11. The process according to claim 1 or claim 2, further comprising the step of reacting butadiene with acetic acid to form the alkoxycarbonyl butene and reacting at least a portion of the pentenoic acid anhydride with water to yield acetic acid and pentenoic acid.

* * * * *